US006268533B1

(12) United States Patent
Gao et al.

(10) Patent No.: US 6,268,533 B1
(45) Date of Patent: Jul. 31, 2001

(54) FORMOTEROL PROCESS

(75) Inventors: Yun Gao, Southborough, MA (US); Robert Hett, Aarau (CH); Kevin Q. Fang, Wellesley, MA (US); Stephen A. Wald, Sudbury, MA (US); Chris Hugh Senanayake, Shrewsbury, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 09/493,042

(22) Filed: Jan. 27, 2000

Related U.S. Application Data

(60) Division of application No. 09/083,010, filed on May 21, 1998, now Pat. No. 6,040,344, which is a continuation-in-part of application No. 08/747,592, filed on Nov. 12, 1996, now abandoned.

(51) Int. Cl.$^7$ .................................................. C07C 217/52
(52) U.S. Cl. .......................... 564/216; 549/520; 549/553; 564/220; 564/221; 564/389; 564/417; 564/447; 568/586
(58) Field of Search ..................................... 564/216, 220, 564/221, 389, 417, 442; 568/586; 549/520, 553

(56) References Cited

FOREIGN PATENT DOCUMENTS

| 390762 | 10/1990 | (EP) . |
| 2005492 | 3/1989 | (ES) . |
| 2031407 | 12/1992 | (ES) . |
| WO92/05147 | 4/1992 | (WO) . |

OTHER PUBLICATIONS

Hett et al. "Large Scale Synthesis of Enantio– and Diastereomerically Pure (R,R)–Formoterol" *Organic Proc. Res. & Dev.* 2, 96–99 (1998).

Hett et al. "Conformational Toolbox of Oxazaborolidine Catalysts in the Enantioselective . . . " *Tet. Lett.* 39, 1705–1708 (1998).

Hett et al. "Enantio– and Diastereoselective Synthesis of all Four Stereoisomers of Formoterol" *Tet. Lett.* 38, 1125–1128 (1997).

Murase et al. "New β–Adrenoreceptor Stimulants. Studies on 3-Acylamino–4–hydroxy– . . . " *Chem. Pharm. Bull.* 25(6), 1368–1377 (1977).

Murase et al. "Absolute Configurations of Four Isomers of 3—Formamido—4 —hydroxy—. . . " *Chem. Pharm. Bull.* 26(4), 1123–1129 (1978).

Trofast et al. "Steric Aspects of Agonism and Antagonism at β–Adrenoceptors: Synthesis . . . " *Chirality* 3, 443–450 (1991).

Kurihara et al. "(–)+–Formoterol, † a Selective $\beta_2$—Adrenoreceptor Agonist" *Acta Cryst.* C53, 1887–1889 (1997).

*Primary Examiner*—Richard L. Raymond
(74) *Attorney, Agent, or Firm*—Heslin & Rothenberg, P.C.

(57) ABSTRACT

A method is disclosed for the preparation of optically pure isomers of formoterol by the reaction of an optically pure 4-benzyloxy-3-formamidostyrene oxide with an optically pure 4-methoxy-α-methyl-N-(phenylmethyl) benzeneethanamine followed by debenzylation. Useful intermediates in the process are also disclosed, as are the novel L-tartrate salt of R,R-formoterol and pharmaceutical compositions thereof.

20 Claims, No Drawings

FORMOTEROL PROCESS

CROSS REFERENCE TO RELATED APPLICATIONS

This application is a divisional of prior application Ser. No. 09/083,010, filed May 21, 1998, now U.S. Pat. No. 6,040,344, which was a continuation-in-part of application Ser. No. 08/747,592, filed Nov. 12, 1996, now abandoned, the entire disclosures of which are incorporated herein by reference.

FIELD OF THE INVENTION

The present invention relates to a method of preparation of optically pure isomers of formoterol, to specific salts of formoterol and polymorphs thereof and to their use in pharmaceutical compositions.

BACKGROUND OF THE INVENTION

Formoterol, whose chemical name is (+/−) N-[2-hydroxy-5-[1-hydroxy-2[[2-(p-methoxyphenyl)-2-propyl]amino]ethyl]phenyl]-formamide, is a highly potent and $\beta_2$-selective adrenoceptor agonist having a long lasting bronchodilating effect when inhaled. The structure of formoterol is as shown:

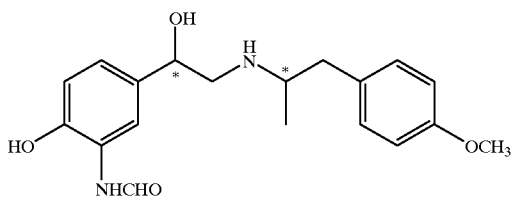

Formoterol has two chiral centers in the molecule, each of which can exist in two possible configurations. This gives rise to four combinations: (R,R), (S,S), (R,S) and (S,R). (R,R) and (S,S) are mirror images of each other and are therefore enantiomers; (R,S) and (S,R) are similarly an enantiomeric pair. The mirror images of (R,R) and (S,S) are not, however, superimposable on (R,S) and (S,R), which are diastereomers. Formoterol is available commercially only as a racemic diastereomer, (R,R) plus (S,S) in a 1:1 ratio, and the generic name formoterol refers to this enantiomeric mixture. The racemic mixture that is commercially available for administration is a dihydrate of the fumarate salt.

The graphic representations of racemic, ambiscalemic and scalemic or enantiomerically pure compounds used herein are taken from Maehr *J. Chem. Ed.* 62, 114–120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, the formula for formoterol above reflects the racemic nature of the commercial material, while among the structures below, those having open wedges are intended to encompass a pure, single configuration which is one of the two possible at that carbon, and those having solid wedges are intended to encompass the single, pure isomer having the absolute stereochemistry shown.

All four isomers of formoterol have been synthesized and briefly examined for relaxing activity on the guinea pig trachea [Murase et al., *Chem. Pharm. Bull.* 26, 1123–1129 (1978). It was found that the (R,R)-isomer is the most potent, while the others are 3–14 times less potent. More recently, the four isomers have been examined with respect to their ability to interact in vitro with β-adrenoceptors in tissues isolated from guinea pig [Trofast et al., *Chirality* 3, 443–450 (1991)]. The order of potency was (R,R)>>(R,S)=(S,R)>(S,S). It was found that the (R,R)-isomer is 1000-fold more potent than the (S,S)-isomer. Preliminary research indicates that administration of the pure (R,R)-isomer may offer an improved therapeutic ratio.

Two reports have been published describing the synthesis of all four isomers of formoterol. In the first report [Murase et al op. cit.], the (R,R)- and (S,S)-isomers were obtained by diastereomeric crystallization of racemic formoterol with tartaric acid. In the second report [Trofast et al. op. cit.], racemic 4-benzyloxy-3-nitrostyrene oxide was coupled with an optically pure (R,R)- or (S,S)-N-(1-phenylethyl)-N-(1-(p-methoxyphenyl)-2-propyl)amine to give a diastereomeric mixture of formoterol precursors, which were then separated by semipreparative HPLC and transformed to the pure formoterol isomers. Both syntheses suffer long synthetic procedure and low overall yield and are impractical for large scale production of optically pure (R,R)- or (S,S)-formoterol. For example, the Trofast reference describes reacting 4.5 grams of the styrene oxide with 4.8 grams of the phenethylamine to produce 94 milligrams of the pure S,S enantiomer. Therefore, there exists a need for a more economical and efficient method of making optically pure formoterol.

SUMMARY OF THE INVENTION

The processes of the invention provide a practical synthesis of optically pure formoterol, for example, (R,R)- and (S,S)-formoterol:

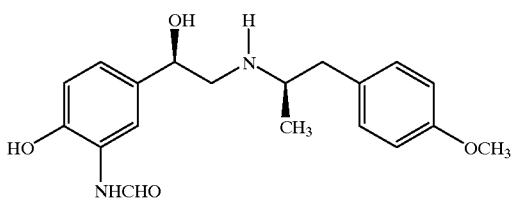

R,R-formoterol

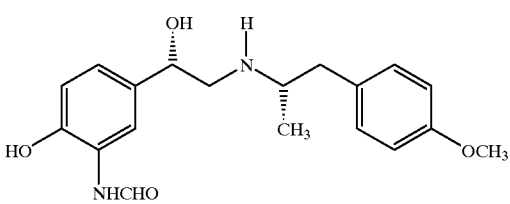

S,S-formoterol

In its broadest aspect, the invention relates to a process for preparing a compound of formula F

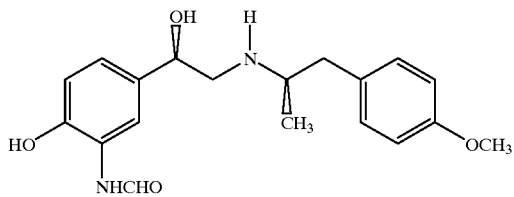

F

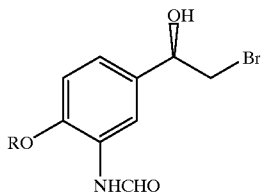

by treatment with a base, and the benzylamine may be produced in situ from a corresponding salt by treatment with a base. In one embodiment, the steps may be combined to provide a process wherein a compound of formula FBH3:

or a salt thereof, comprising the sequential steps of: (a) reacting a compound of formula

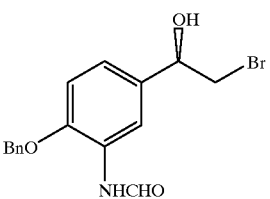

FBH3 wherein R is benzyl or substituted benzyl, with a compound of formula FBA:

a compound of formula FBA-HA:

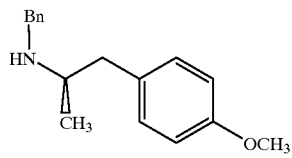

FBA

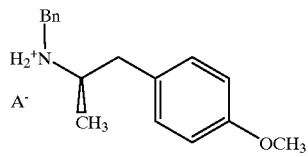

FBA-HA and (b) reducing with hydrogen gas in the presence of a noble metal catalyst.

The term "substituted benzyl" refers to any protecting group for a phenol that contains the benzyl (or phenylmethyl) nucleus substituted with one or more substituents that do not interfere with its function as a protecting group. Suitable substituents include: $C_1$ to $C_6$-alkyl, $C_1$ to $C_6$-alkoxyl, halogen and combinations thereof. In a particular embodiment, R is benzyl (Bn), and the compound is referred to herein as FAE:

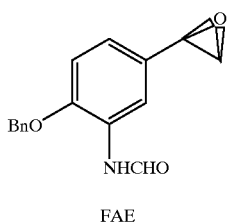

FAE

The epoxide may be produced in situ from the corresponding bromohydrin:

and at least one equivalent of a base are combined to produce a mixture comprising an epoxide and a free base. The mixture of epoxide and free base is heated at a temperature sufficient to cause a reaction to produce a benzyl-protected aminoalcohol, and the benzyl-protected aminoalcohol is reduced with a source of hydrogen in the presence of a noble metal catalyst. In the above structure $A^-$ is the anion of a conjugate acid HA having a pKa sufficient to protonate the amine.

In the foregoing processes a preferred noble metal catalyst is palladium and a preferred base is an alkali metal carbonate, particularly potassium carbonate. The source of hydrogen may be hydrogen gas or a hydrogen-donating compound such as ammonium formate.

Suitable acid addition salts for the compounds of the present invention include for example, acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. The mandelic acid salt is especially preferred for compounds of formula FBA; the tartrate and fumarate are preferred for formoterol enantiomers F.

In another aspect, the invention relates to a process for synthesizing a compound of formula

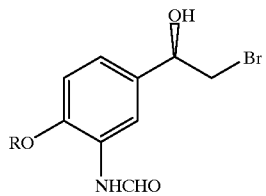

comprising the sequential steps of (a) reducing 2-bromo-4'-RO-3'-nitroacetophenone with about one equivalent of a borane reagent in the presence of a catalytic amount of a single enantiomer of an oxazaborolidine reagent derived from a chiral aminoalcohol, preferably from cis 1-amino-2-indanol, to produce substantially enantiomerically pure α-(bromomethyl)-4-RO-3-nitrobenzenemethanol:

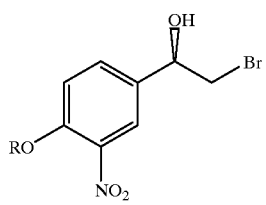

(b) reducing the α-(bromomethyl)-4-RO-3-nitrobenzenemethanol with hydrogen in the presence of a noble metal catalyst to produce an aniline; and (c) formylating the aniline with formic acid and acetic anhydride. A preferred noble metal catalyst for this process is platinum. Steps (b) and (c) may be carried out without isolation of the aniline. In a preferred embodiment, R is benzyl and 2-bromo-4'-benzyloxy-3'-nitroacetophenone is reduced to produce substantially enantiomerically pure α-(bromomethyl)-4-phenylmethoxy-3-nitrobenzenemethanol (FBH):

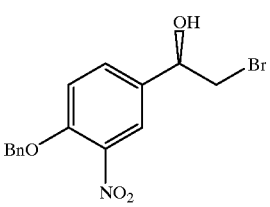

In a more preferred embodiment the single enantiomer of an oxazaborolidine is derived from (1R,2S)-1-amino-2-indanol, which produces α-(bromomethyl)-4-phenylmethoxy-3-nitrobenzenemethanol of the R configuration. The oxazaborolidine may be generated in situ from (1R,2S)-1-amino-2-indanol and two equivalents of borane-THF or borane-methyl sulfide.

In another aspect, the invention relates to a process for preparing a substantially enantiomerically pure salt of 4-methoxy-α-methyl-N-(phenylmethyl)benzeneethanamine of formula FBA-HA

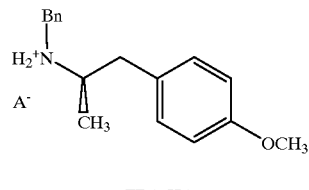

comprising: (a) reducing 4-methoxyphenyl acetone with hydrogen in the presence of a platinum catalyst and about 1 equivalent of benzylamine in methanol; (b) adding about one equivalent of a single enantiomer of mandelic acid, (c) heating to obtain a methanolic solution; (d) cooling to obtain a crystalline solid phase; and (e) recovering the crystalline solid from the methanolic solution. If desired, one may convert the crystalline mandelic acid salt from step (e) to a salt of an acid other than mandelic acid by processes well known in the art.

In another aspect, the invention relates to an overall process for preparing a compound of formula F:

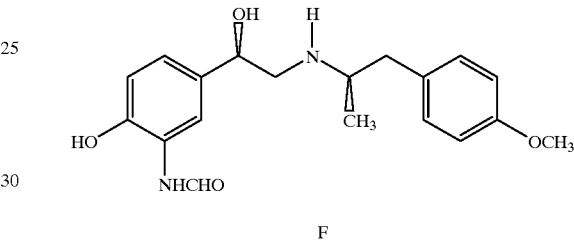

from 2-bromo-4'-benzyloxy-3'-nitroacetophenone and 4-methoxy-α-methyl-N-(phenylmethyl)benzeneethanamine comprising the sequential steps of: (a) reducing 2-bromo-4'-benzyloxy-3'-nitroacetophenone with about one equivalent of a borane reagent in the presence of a catalytic amount of a single enantiomer of an oxazaborolidine derived from cis 1-amino-2-indanol to produce substantially enantiomerically pure α-(bromomethyl)-4-phenylmethoxy-3-nitrobenzenemethanol (FBH); (b) reducing the α-(bromomethyl)-4-phenylmethoxy-3-nitrobenzenemethanol with hydrogen in the presence of a noble metal catalyst to produce an aniline FBH2; (c) formylating the aniline with formic acid and acetic anhydride to produce a compound of formula FBH3:

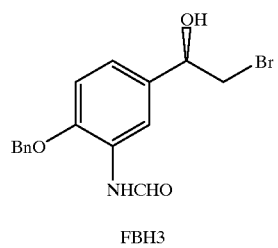

(d) combining FBH3, a salt of 4-methoxy-α-methyl-N-(phenylmethyl)benzeneethanamine (FBA-HA) and at least one equivalent of a base to produce a mixture comprising an epoxide (FAE) and a free base (FBA); (e) heating the mixture of epoxide and free base at a temperature sufficient to cause a reaction to produce a benzyl-protected aminoalcohol (DBF); and (f) reducing the benzyl-protected aminoalcohol with hydrogen gas in the presence of a noble metal catalyst.

In another aspect, the invention relates to compounds of formula:

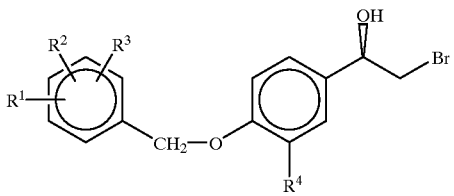

wherein each of $R^1$, $R^2$ and $R^3$ is independently chosen from the group consisting of hydrogen, $C_1$ to $C_6$-alkyl, $C_1$ to $C_6$-alkoxyl, and halogen and $R^4$ is —$NO_2$, —$NH_2$ or —NHCHO. The compounds are useful as intermediates in the synthesis of single enantiomers of formoterol. The compounds in which all of $R^1$, $R^2$ and $R^3$ are hydrogen are preferred.

In another aspect, the invention relates to the L-(+)-tartrate salt of R,R-formoterol, which is unexpectedly superior to other salts of R,R-formoterol in that it is easy to handle, pharmaceutically acceptable and non-hygroscopic. The L-(+)-tartrate salt of R,R-formoterol exists in two polymorphic forms, each of which has certain advantages.

In another aspect, the invention relates to a pharmaceutical composition comprising R,R-formoterol L-(+)-tartrate and a pharmaceutically acceptable carrier. In one embodiment the carrier is substantially lactose-free. By "substantially lactose-free" it is meant that there is either no lactose or insufficient lactose present to cause any measurable increase in the rate of loss of formoterol as a function of time, temperature and humidity. The compositions include aerosol pharmaceutical compositions, oral pharmaceutical compositions, such as tablets, capsules and syrups, and dry powder pharmaceutical compositions. The dry powder compositions for inhalation comprise R,R-formoterol L-(+)-tartrate and a dry, solid carrier, such as lactose, having a mean particle size between 1 μm and 100 μm.

DETAILED DESCRIPTION

The present invention relates to a more practical and efficient process for the preparation of optically pure isomers of formoterol. This method is particularly advantageous in comparison with known methods because it utilizes optically pure precursors that are readily available by simple resolution and asymmetric reduction. The overall sequence is set forth in Scheme 1, wherein R has been exemplified as benzyl. The same sequence could be used to produce other intermediates in which R is substituted benzyl by beginning with the appropriate starting material analogous to FBK. Brackets indicate intermediates that could be isolated but are not usually isolated in the integrated process.

Scheme 1

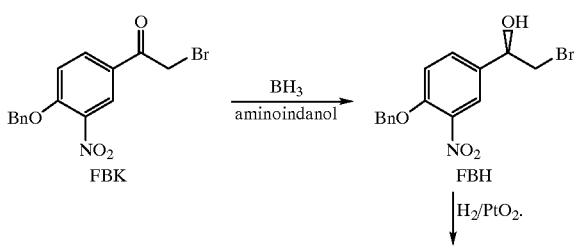

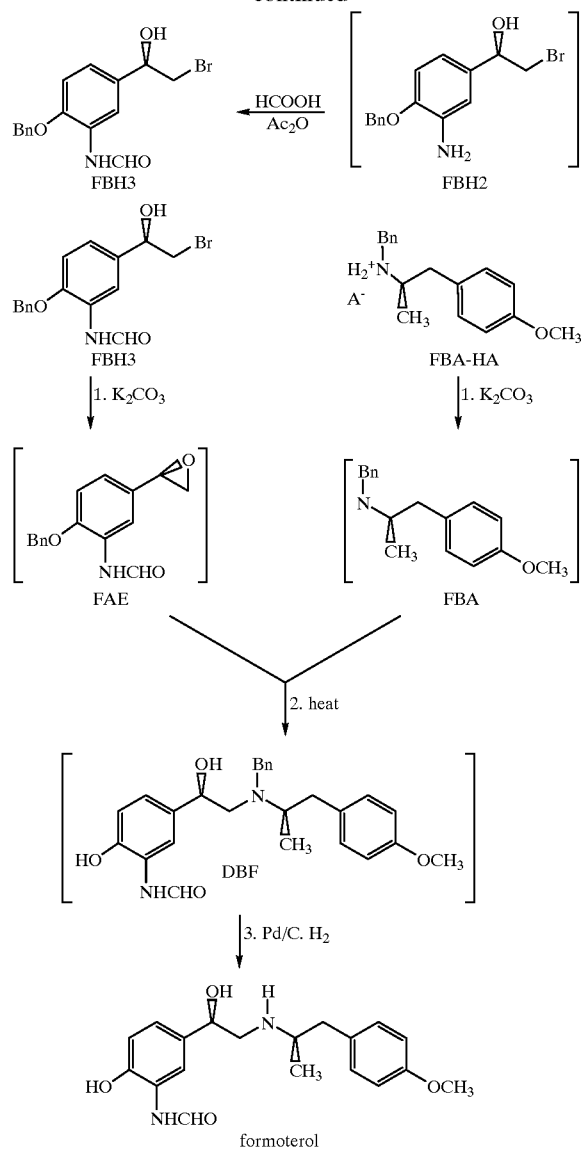

In the process described above, the optically pure 4-methoxy-α-methyl-N-(phenylmethyl)benzene-ethanamine, also called 2-N-benzylamino-1-(p-methoxyphenyl)propane (FBA), is obtained by resolution of the racemic compound with L- or (D)-mandelic acid using a modification of the procedure of Kraft, et al. [Rec. Trav. Chim. Pays-Bas 85, 607 (1966)]. The racemic N-benzylamine compound was prepared by the reductive amination of p-methoxyphenylacetone with N-benzylamine under catalytic hydrogenation, but other reductive conditions using methods known in the art could be used. (See, Houben-Weyl's Methoden der Org. Chem. Band IV/1c, p427.)

The invention encompasses a process for making optically pure formoterol from optically pure 4-benzyloxy-3-formamidostyrene oxide (FAE) comprising the coupling and hydrogenation described above in combination with a method for the preparation of the optically pure styrene oxides. According to this aspect the optically pure styrene oxide is obtained by: (a) reduction of 2'-bromo-4-benzyloxy-3-nitroacetophenone with a borane reagent stereoselectively in the presence of a chiral oxazaborolidine catalyst to give the corresponding optically active bromohydrin [See, Hong, et al., *Tetrahedron Lett.* 35, 6631(1994)] and U.S. Pat. No. 5,495,821]; (b) reduction of the 3-nitro group to the amino group followed by formylation with formic acid or formic acid/acetic anhydride ($Ac_2O$) to give the 3-formamido bromohydrin FBH3; and (c) conversion of the 3-formamido bromohydrin to the corresponding 4-benzyloxy-3-formamidostyrene oxide FAE with a base.

The optically pure 2-N-benzylamino-1-(p-methoxyphenyl)propane (FBA) is obtained by resolution of the racemic compound with L- or (D)-mandelic acid. The resolution of racemic NV-benzylamine compound is performed using one equivalent of L- or D-mandelic acid in an alcohol solvent such as methanol (MeOH). Optically pure benzylamine mandelic acid salt (FBA-MA) is obtained after four or five crystallizations. The free V-benzylamine compound is then obtained by treating the mandelic acid salt with a base such as aq. NaOH or aq. $Na_2CO_3$ or aq. $NH_3$ in the presence of an inert organic solvent such as t-butyl methyl ether (MTBE) or ethyl acetate (EtOAc) followed by evaporation of the solvent. (R)-2-N-benzylamino-1-(p-methoxyphenyl)propane is obtained from the L-(+)-mandelic acid salt while the (S)-enantiomer is obtained from the D-(−)-mandelic acid salt. From the same lot of racemic N-benzylamine compound, both (R)- and (S)-enantiomer can be obtained by using the appropriate mandelic acid.

The optically pure epoxide (FAE) is prepared from commercially available 4-benzyloxy-3-nitroacetophenone. Thus, the acetophenone may be brominated with bromine or pyridinium tribromide in an inert organic solvent such as $CH_3CN$, MeOH or chloroform to give the α-bromoacetophenone. The bromoacetophenone is then reduced with a borane reducing agent, such as $BH_3.THF$, $BH_3$.diethylaniline or $BH_3Me_2S$, in the presence of a chiral oxazaborolidine catalyst, such as cis-(1R,2S)-aminoindanol-B-Me catalyst, to give the optically active bromohydrin after isolation by crystallization in >96% ee. The bromohydrin can be further enriched to >98% ee by recrystallization. The absolute configuration of the bromohydrin is determined by the chirality of the oxazaborolidine catalyst. The nitro group in the bromohydrin is selectively reduced to the amine group using a reducing agent known for selective nitro reduction, such as Sn, Fe with acid, $SnCl_2$ or by heterogeneous catalytic hydrogenation in the presence of a noble metal catalyst such as $PtO_2$ or Pt/C. Catalytic hydrogenation is cleaner if a noble metal catalyst such as platinum on carbon poisoned with dimethyl sulfide is used. The amine group is then formylated with a mixture of formic acid and acetic anhydride without racemization, and the resulting compound is converted to optically pure 4-benzyloxy-3-formamidostyrene oxide with a base such as aq. NaOH or $K_2CO_3$ in an alcohol solvent or solvent mixture such as MeOH/THF. The epoxide obtained can be purified by recrystallization from an inert organic solvent or solvent mixture, preferably from EtOAc/heptane or toluene/heptane.

The optically pure 2-N-benzylamino-1-(p-methoxyphenyl) propane (FBA) is reacted with optically pure 4-benzyloxy-1-formamidostyrene oxide without racemization to give an optically pure N,O-di-benzylformoterol intermediate (DBF), and the N,O-di benzyl group of the dibenzylformoterol is removed by hydrogenation in the presence of a hydrogenation catalyst, to give optically pure formoterol. Alternatively, the dibenzylformoterol is obtained directly from the reaction of optically pure 2-N-benzylamino- 1-(p-methoxyphenyl)propane with the optically pure 1-(4'-benzyloxy-3'-formamidophenyl)-2-bromoethanol (FBH3) in the presence of a base whereby the epoxide (FAE) is formed in situ.

For the synthesis of optically pure formoterol, the optically pure N-benzylamine sidechain may be coupled with the epoxide without solvent at temperature in the range of 100–140° C., or in a high boiling inert solvent under reflux. Suitable solvents include toluene, t-butanol, t-amylalcohol, and methyl isobutylketone (MIBK). The resulting dibenzylformoterol (DBF) can be purified by column chromatography or by recrystallization as salt of an organic acid such as fumaric acid. It can also be used directly without purification for the de-benzylation reaction to form formoterol.

The dibenzylformoterol product is converted by catalytic hydrogenation in the presence of Pd catalyst such as Pd/C directly to optically pure formoterol. This reaction is preferably performed in an alcohol solvent such as methanol, ethanol, or 2-propanol at 40–60 psi of hydrogen pressure and 15–30° C. for 2–15 hours. Although the formoterol product can be isolated as the fumaric acid salt by adding fumaric acid to the reaction solution after removal of the catalyst, a product of higher purity is obtained if the for-moterol is recovered and purified as the tartrate salt and then converted to the fumarate. Alternatively, the hydrogenation (de-benzylation) can be performed in the presence of the appropriate organic acid in an alcohol solvent such as MeOH under similar conditions. The resulting formoterol acid salt is then isolated by crystallization by addition of a less polar co-solvent after filtration to remove the catalyst.

In a specific synthesis, the enantioselective reduction of FBK was done with 15 mol % AIBMe catalyst at −15° C. The bromohydrin was isolated after aqueous work-up with enantioselectivities ranging from 96–98% isomeric purity. The catalyst AIBMe was generated from aminoindanol and trimethylboroxine, followed by azeotropic removal of by-products using toluene. When the FBH was not purified by crystallization, 2–4% of minor isomer was carried through the synthetic sequence and caused lower yields in the last step. In those cases it was necessary to crystallize with L-tartaric acid 3–4 times at the last step in order to obtain the desired enantiomeric purity (>99.5%) of formoterol tartaric acid salt.

The chiral amine, 4-methoxy-α-methyl-N-(phenylmethyl)benzeneethanamine, was synthesized by a reductive amination procedure followed by a novel resolution procedure with mandelic acid. A concentration of 0.4M appears to be the optimal concentration and provides the product after 3–4 crystallizations in isomeric purities of 99.5–100%.

In Scheme 1, the aniline (FBH2) can be isolated as an intermediate and then transformed to the epoxide, but FBH2 has a tendency to oxidize when exposed to air. Therefore, there is an advantage to not isolating the FBH2 and instead hydrogenating in THF, which allows the formylation directly after filtration of the catalyst. The formamidobromohydrin (FBH3), as a highly crystalline compound, can be isolated from the reaction mixture without aqueous work-up. Using pure FBH3 and forming the epoxide provides crystalline FAE.

The epoxide opening reaction was conducted as neat reaction with the free amine to give the penultimate precursor dibenzylformoterol (DBF), as an oil with a purity of 85–87%. The reaction may also be run in toluene, 2-propanol or t-amyl alcohol.

Crude DBF can be converted to formoterol tartrate, which can be crystallized in high yields and high purities, and formoterol fumarate can be generated by salt switch from the purified formoterol tartrate. Although formoterol fumarate can also be crystallized directly from the hydrogenation mixture in high yields, subsequent crystallizations do not remove a major impurity.

In the enantioselective reduction of FBK to FBH, an AIBMe catalyst consistently gives slightly higher selectivities than the AIBH, but it is more difficult to prepare, more expensive and the optimum process temperature is lower than that of the AIBH process.

Epoxide formation from FBH3 and release of the free base from the benzylamine FBA-HA may be accomplished in separate steps. However, since both reactions require a base, a combination of both steps into a one pot procedure is possible and simplifies the process.

Experimental

2-Bromo-4'-benzyloxy-3'-nitroacetophenone (FBK)

A 5-liter flask was charged with 300 g (1.1 mol) of 4-benzyloxy-3-nitroacetophenone and 3 liters of acetonitrile. The mixture was heated to 50° C. to form a clear solution, and 180 g of bromine (1.6 mol) was added in one portion. The reaction was stirred at 50° for 15–25 minutes, during which time the deep red color changed to pale orange and TLC (ethyl acetate/hexane 3:7) showed no remaining starting material. Without heating, 200 to 300 mL of acetonitrile, along with the byproduct hydrogen bromide, were distilled from the reaction under vacuum. During the course of the distillation, the temperature dropped to about 15° and the product precipitated as a yellow solid. The reaction was stirred at 0–5° for two hours and the product filtered off and washed with acetonitrile. The resulting 2-bromo 4'-benzyloxy-3'nitroacetophenone was dried in vacuum to yield 242 g (63%) of off-white solid having a melting point of 136° C.

In an improved procedure, bromine was replaced by pyridinium tribromide and the bromination was carried out at room temperature. The product was isolated by addition of water.

R-α-(bromomethyl)-4-phenylmethoxy-3-nitrobenzemethanol (FBH)

A 2-liter flask was charged with 2.5 g (17 mmol) of (1R,2S)-aminoindanol in 50 mL of THF under argon. While cooling to maintain a temperature below 25° C., 3.4 mL (34 mmol) of a 10 mol solution of borane methyl sulfide was added over a period of 5 minutes and the reaction stirred for ten minutes at 25° C. to complete formation of the catalyst. To this catalyst solution the ketone and reducing agent were added simultaneously. From separate reservoirs were added (1) a solution of 120 g of FBK (0.34 mol) in 950 mL of THF and (2) 24 mL of 10 M borane-methyl sulfide. Addition was over a period of 3 hours at 25° C. The reaction was cooled on an ice bath and 100 mL of methanol was added over a period of 15 minutes. The reaction mixture was concentrated under vacuum to a volume of about 200 mL, and 650 mL of toluene was added to dissolve the residue. The solution was washed with 0.2 M sulfuric acid and then water. If desired the aminoindanol may be recovered from the aqueous acidic phase. The organic phase was dried over sodium sulfate, filtered and concentrated to a weight of 240–260 g. A total of 100 mL of heptane was added to the mixture with stirring at 50–60°, then cooled to 15–20° and filtered. Although the wet filter cake may be used in the next step without drying, the solid was dried under vacuum to give 95–108 g of (R)-FBH as an off white solid, melting point 68° C.

An alternative reduction employed borane-THF. The reduction was carried out at 2–5° C. instead of 25° C. and quenched with acetone instead of methanol. Yields were comparable to the process with $BH_3.DMS$, as long as the borane titre in the $BH_3.THF$ was high.

N-[5-(2-bromo-1-hydroxyethyl)-2-(phenylmethoxy)phenyl] formamide (FBH3)

A solution of 100 g (0.28 mol) of (R) FBH in 200 mL of THF and 200 mL of toluene was hydrogenated in a Parr hydrogenator in the presence of 1 g of platinum oxide catalyst at 45–50 psi for 7–13 hours until hydrogen uptake ceased. The reaction mixture was filtered through a bed of diatomaceous earth and a solution of 21.5 g (0.48 mol) of formic acid and 33 g (0.32 mol) of acetic anhydride, which had been pre-mixed, was added to the filtrate, which was maintained at 10–15° C. by external cooling. The solution was stirred for 20 minutes at 10–25° C. and then concentrated to about 300 mL at 30° C. One hundred milliliters of toluene was added and the reaction was stirred at 15° C. for 15 minutes. The resulting slurry was filtered to provide 75 g (76% yield of (R)-FBH3 melting point 130° C., isomeric purity 99–99.5%. The product is also sometimes referred to as 2-bromo-(4'-benzyloxy-3'-formamidophenyl)ethanol.

An alternative reduction using 6 g of 10% platinum on carbon and 0.12–0.5 g of dimethyl sulfide, with no toluene, gave cleaner product when $BH_3.THF$ was used as the reducing agent in the previous step. The use of 30 g of formic acid to prepare the mixed anhydride was found to improve yields.

N-[5-oxiranyl-2-(phenylmethoxy)phenyl]formamide (FAE)

If it is desired to isolate the epoxide, as opposed to generating it in situ in the next step, the following procedure may be used: a solution of 28 g of the aniline FBH2 from platinum catalyzed reduction of the nitro compound FBH was treated with a mixture of 17 mL of the mixed formic/acetic anhydride, concentrated to dryness and dissolved in 200 mL of methanol. The methanolic solution was treated with 60 g of potassium carbonate, stirred at 30 minutes and concentrated under vacuum. The resulting residue was triturated with 400 mL of ethyl acetate, washed with water and brine, decolorized with carbon and dried over sodium sulfate. The drying agent and carbon were filtered off and the filtrate concentrated to give 19.3 g (86% yield) of the epoxide FAE as an oil, which solidified on standing (95.4% ee; m.p. 64–65° C.).

(R,R)-Formoterol-L-tartrate

A 2-liter flask was charged with 70 g of (R)FBH3 (0.2 mol) 76.5 g of (R)-FBA-L-MA (0.19 mol), 70 g of potassium carbonate (0.5 mol), 400 mL of THF and 400 mL of methanol. The mixture was stirred at 25° for 1–2 hours and the reaction followed by HPLC. When the starting material (FBH3) content was below 2%, the mixture was concentrated to dryness at 30–35° C. under vacuum. To the residue were added in order, first 600 mL of toluene and then 600 mL of water. The slurry was stirred 10 minutes, the phases were separated and the organic phase was dried over sodium sulfate. The toluene solution was filtered free of drying agent and concentrated to 110 g. The residue, which was shown by HPLC to be a 1:1 mixture of FAE and FBA, was stirred under argon atmosphere at 110–130° C. for 24 hours. To the hot mixture was added 400 mL of ethanol to obtain a clear solution of (R,R)DBF. The solution was cooled to 25°, transferred to a Parr hydrogenator and hydrogenated at 45–50 psi in the presence of 10 g of 5% palladium on carbon until hydrogen uptake was complete (3–4 hours). The mixture was filtered through a pad of diatomaceous earth washed with 200 mL of 2-propanol, and 28.5 g of L-tartaric acid (0.19 mol) and 60 mL of water was added to the filtrate. The mixture was heated to 60–80° C. until a clear solution was formed. As soon as the clear solution formed, heating was discontinued and the mixture was cooled to 25°, at which temperature it was held for 1–2 hours. It was then further cooled to 0–5° for 1 hour and the product collected by filtration. The product was dried under vacuum to provide 70–80 g of (R,R) formoterol L-tartrate as an off white powder. The tartrate salt was dissolved in 700–800 mL of hot 80% aqueous 2-propanol, cooled as before and filtered again. The second recrystallization provided 60–70 g of (R,R) formoterol L-tartrate as an off-white powder having a melting point between 179 and 184 depending upon purity. A product having a chemical purity of 99.8% and an enantiomeric purity of 99.7% exhibits a melting point of 184° C.

The hydrogenation was found to be improved by replacing ethanol with a mixture of toluene and 2-propanol as the solvent. This was accomplished by cooling the condensation reaction to 100° C., adding toluene to 5M, then cooling to 70–75° C. and adding 2-propanol to 1M.

(R,R) formoterol L-tartrate appears to crystallize in two distinct polymorphs. The first polymorph, which we will refer to as P1, in pure form exhibits a peak at about 193° C. on differential scanning calorimetry and is soluble in water at 25° C. to the extent of 15.4 mg/mL; the second polymorph, which we will refer to as P2, in pure form exhibits a peak at about 179° C. on differential scanning calorimetry and is soluble in water at 25° C. to the extent of 26.7 mg/mL. To obtain (R,R) formoterol L-tartrate of the highest chemical and optical purity, it is necessary that one not recrystallize P1. P1 is the more thermodynamically stable form and is preferred for formulations, but because of its lower solubility, it requires higher temperatures and longer times to dissolve in the recrystallization solvent. As a result, some degradation occurs and impurities are introduced in the recrystallization process.

To take advantage of the greater stability of the P1 polymorph but avoid its recrystallization, the workup described above was modified. If aqueous tartaric acid was added to the solution of hydrogenation product in 128 mL of 80:20 (v/v) 2-propanol/toluene, and the mixture was stirred for 2 hours, the initially crystallized material was predominantly or exclusively P2. It can be converted to P1 by warming in solution to 52–55° C. and seeding with P1. Alternatively, 1 equivalent of tartaric acid in water (4.2 mL/g of tartaric acid) was added to formoterol free base in 80:20 (v/v) THF/toluene (10.8 mL/g of free base) at room temperature and the mixture was stirred for 18 hours. The material that was filtered off was pure polymorph P1.

(R,R) Formoterol Fumarate

A 2-liter flask was charged with 650 mL of water and 60 g of (R,R) formoterol L-tartrate (0.12 mol). The mixture was stirred and 52 g of sodium bicarbonate (0.6 mol) was added in small portions. The product was extracted into 250 mL of ethyl acetate, dried over sodium sulfate, filtered and concentrated to give 56 g of the free base. The free base was dissolved in 260 mL of isopropyl alcohol and 7.0 g of fumaric acid (60 mmol) was added followed by 130 mL of 2-propanol. The mixture was heated to 50–60° until a clear solution was formed and then cooled as above to crystallize the fumarate salt. The product was filtered and washed with 2-propanol to provide 44 g of (R,R) formoterol fumarate as white crystals having a chemical purity greater than 98% and an enantiomeric purity greater than 99.5%.

4-Methoxy-α-methyl-N-(phenlymethyl)benzene ethanamine L-mandelic acid salt (FBA-L-MA)

To 800 mL of methanol were added 328 g of 4-methoxyphenylacetone (2 mol) and 214 g of N-benzylamine (2 mol). The imine formation was exothermic and the solution warmed to 45° C. After reaction was complete, the solution was hydrogenated at 50 psi for 6–8 hours in the presence of 3.3 g of 5% platinum on carbon catalyst. When the hydrogen uptake had stopped, the reaction was filtered through diatomaceous earth, and the filter cake was washed with 200 mL of methanol. The combined filtrates were placed in a 6-liter flask and diluted with 4.2 liters of methanol. Three hundred four grams of (S)-L-mandelic acid (2 mol) was added and the mixture heated with stirring to reflux to obtain a clear solution. The solution was cooled to room temperature, stirred at room temperature for two hours and the mandelic acid salt filtered off. The recrystallization was repeated three times to obtain 60–70 g, of (R)-FBA-L-MA having, isomeric purity greater than 99.8% and a melting point of 164° C.

Water absorption is a major problem in formulating a medicament for therapeutic use, and therefore a salt that has minimal water absorption offers significant advantages. In a series of experiments various salts of R,R-formoterol were prepared. The salts prepared were: (1) the hydrochloride; (2) the sulfate; (3) the fumarate; (4) the D-tartrate; and (5) the L-tartrate (P1 polymorph).

The salts were exposed to varying levels of humidity at room temperature for 1 to 28 days, and the samples were analyzed for water content by Karl Fischer titration. The results are shown in Tables 1–5 below. The values are given in % w/w.

TABLE 1

Moisture Sorption fo (R,R)-Formoterol-HCl

| | Relative Humidity | | | |
|---|---|---|---|---|
| Day | 11% | 43% | 75% | 89% |
| 1 | 0.5735 | 0.8502 | 1.5335 | 1.4573 |
| 3 | 0.553 | 1.1636 | 1.3288 | 2.419 |
| 8 | 0.3656 | 0.8781 | 1.4931 | 1.6487 |
| 14 | 0.4385 | 0.9802 | 1.4585 | 1.5739 |
| 28 | 0.2644 | 0.8133 | 1.221 | 1.1139 |

TABLE 2

Moisture Sorption For (R,R)-Formoterol-SO$_4$

| | Relative Humidity | |
|---|---|---|
| Days | 11% | 43% |
| 1 | 1.2251 | 2.9647 |
| 3 | 1.3892 | 3.4998 |
| 8 | 0.9574 | 3.4048 |
| 14 | 1.209 | 2.2985 |
| 28 | 0.7866 | 3.1595 |

TABLE 3

Moisture Sorption for R,R-Formoterol Fumarate

| | Relative Humidity | | | | |
|---|---|---|---|---|---|
| Day | 33% | 43% | 77% | 85% | 95% |
| 1 | 1 | 1 | 1 | 8 | 13.5 |
| 2 | 1 | 1 | 1 | 6 | 16 |
| 3 | 1 | 1 | 1 | 6 | >16 |
| 7 | 1 | 1 | 1 | 6 | >16 |
| 14 | 1 | 1 | 1 | 6 | >16 |

TABLE 4

Moisture Sorption For (R,R)-Formoterol-(L)-Tartrate

| | Relative Humidity | | | | |
|---|---|---|---|---|---|
| Days | 11% | 43% | 75% | 89% | 93% |
| 1 | 0.0956 | 0.1091 | 0.0895 | 0.1144 | 0.1346 |
| 3 | 0.1062 | 0.1406 | 0.1367 | 0.1379 | 0.2077 |
| 8 | 0.0842 | 0.0922 | 0.0732 | 0.1104 | 0.1076 |
| 14 | 0.1377 | 0.104 | 0.1146 | 0.1097 | 0.2972 |
| 28 | 0.0871 | 0.0705 | 0.0691 | 0.1122 | 0.1765 |

TABLE 5

Moisture Sorption of (RR)-Formoterol-(D)-Tartrate

| Days | 85% Relative Humidity |
|---|---|
| 1 | 0.4399 |
| 3 | 0.531 |
| 8 | 0.4461 |
| 14 | 0.4858 |
| 28 | 0.4034 |

From the foregoing figures it can be noted that even under the relatively dry conditions of 43% relative humidity (RH), the sulfate (2) absorbed more than 3% by weight water. The fumarate and hydrochloride salts were somewhat better at 43% RE, but the fumarate absorbed 6% at 85% RE and the hydrochloride 1.3–1.4% at 75% RH. The D-tartrate was somewhat better than the hydrochloride, absorbing 0.4–0.5% at 85% RH. The L-tartrate of R,R-formoterol was superior to all of the salts tested, absorbing 0.10 to 0.13% at 89%RH. The superiority of the L-tartrate salt for the R,R enantiomer of formoterol is both significant and unexpected. The two polymorphs of (R,R)-formoterol L-tartrate appear to be equivalent in moisture sorption. Thus both P1 and P2 absorb less than 0.1% at 85% RH for 11 days.

To further elucidate the differences between P1 and P2, a direct comparison of the thermal stability of both crystal forms was undertaken. Tables 6 and 7 show the effects of temperature on the stability of the two crystal forms. In each experiment, the polymorph was warmed from 30° C. to the designated temperature at 10° C./min and held at the designated temperature for 15 minutes. The loss on drying (LOD) was measured, and the appearance of the material was noted. The data clearly show that P1 is more stable than P2. Although at temperatures of 75 and 100° C., P2 had a lower LOD than P1, as the temperature rose, the LOD for P2 increased more rapidly than for P1. At 150° C., the LOD for P2 was more than three times greater than for P1. At 175° C., both crystal forms showed significant LODs, the result of decomposition. The differences in appearance of each crystal form at the designated temperatures were consistent with the changes in LODs.

The two crystal forms of (R,R)-formoterol tartrate were also studied by measuring the total impurities in the material from each of the experiments in Table 6. The data are shown in Table 8. In accord with the data in Table 6, P2 was less stable to higher temperatures than P1. At a temperature of 100° C. and higher, P2 had higher levels of total impurities when compared to P1. At 150° C., P2 had more than four times the quantity of impurities as in P1. At 175° C., both crystal forms were nearly completely decomposed. These data, along with the data in Table 6 indicate that P1 is the more stable crystal form. From the standpoint of formulation stability, this makes P1 the preferred polymorph.

TABLE 6

Loss on Drying of (R,R)-Formoterol Tartrate Crystal Forms PI and P2 as Determined by TGA

| | % LOD by TGA* | | | | |
|---|---|---|---|---|---|
| Temperature (C.) | 75 | 100 | 125 | 150 | 175 |
| Crystal Form P1 | 0.092 | 0.065 | 0.230 | 0.390 | 10.805 |
| Crystal Form P2 | 0.020 | 0.045 | 0.305 | 1.230 | 12.990 |

*Ramp from 30° C. to the designated temperature at 10° C./min and hold at the designated temperature for 15 min.

TABLE 7

Appearance of Sample after TQA Analysis

| Temperature (C.) | 75 | 100 | 125 | 150 | 175 |
|---|---|---|---|---|---|
| Crystal Form P1 | white | white | white | off-white | brown |
| Crystal Form P2 | white | white | off-white | tan | brown |

TABLE 8

Total Impurities of (R,R)-Formoterol Tartrate Crystal Forms P1 and P2 at Various Temperatures

| | % Impurities after TGA | | | | | |
|---|---|---|---|---|---|---|
| Temperature (C.) | 25 | 75 | 100 | 125 | 150 | 175 |
| Crystal Form P1 | 0.41 | 0.43 | 0.48 | 0.54 | 0.74 | 95.54 |
| Crystal Form P2 | 0.43 | 0.43 | 0.53 | 0.89 | 3.18 | 98.83 |

While the L-tartrate salt of the R,R isomer of formoterol is clearly superior to other salts, it is somewhat unstable in the presence of water and lactose. This is quite surprising because it is completely stable in the presence of lactose in the absence of water. As a result, the use of lactose in formulations of R,R-formoterol L-tartrate is to be avoided if there is any chance of encountering moisture over an extended period. Alternatively, if lactose is to be used, as described below, the dry powder must be packaged in such a manner as to exclude moisture. This incompatibility is all the more unexpected because it is not observed with racemic (R,R/S,S) formoterol hemifumarate hydrate (the commercially available form of formoterol). Interestingly, however, the hemifumarate salt of R,R-formoterol (the single enantiomer) is very unstable in the presence of lactose and water. Thus we have found that, although very little degradation occurs in dry lactose formulations, upon the addition of 5% water and storage at 60° C./75%RH for one month, a 5:4 mixture of formoterol salt and lactose showed 95%, recovery of formoterol from racemic (R,R/S,S) formoterol hemifumarate hydrate, 81% from R,R-formoterol L-tartrate and 0.3% from R,R-formoterol hemifumarate.

EXAMPLES

Various embodiments of formulations are described in more detail by means of the following examples of pharmaceutical compositions. These are provided by way of illustration and not by way of limitation.

Example 1

Compressed formoterol tablets may be prepared using conventional wet granulation techniques, such that each dosage unit contains 0.06 mg to 1 mg of R,R-formoterol L-tartrate.

|  | Per tablet | Per 10,000 tablets |
|---|---|---|
| Formoterol tartrate | 0.1 mg | 1 g |
| Starch | 60 mg | 600 g |
| Talc | 12 mg | 120 g |
| Acacia | 12 mg | 120 g |
| Stearic Acid | 1 mg | 10 g |

The acacia and an equal weight of starch is blended to form a paste which is used to granulate the formoterol. The mixture is dried and placed through a mesh screen. The remainder of the material is added and mixed thoroughly. The resulting mixture is compressed into tablets using a $^9/_{32}$-inch (7 mm) punch.

Example 2

Compressed R,R-formoterol L-tartrate tablets may be prepared using conventional dry granulation techniques, such that each dosage unit contains 0.06 mg to 1 mg of formoterol tartrate.

|  | Per tablet | Per 10,000 tablets |
|---|---|---|
| Formoterol tartrate | 0.1 mg | 1 g |
| Starch | 85 mg | 850 g |

The starch is dried to a moisture content of 10% and then thoroughly mixed with the formoterol tartrate. The resulting mixture is compressed into slugs and then ground to fine mesh size. Tablets are then compressed, using a $^9/_{32}$-inch (7 mm) punch.

Example 3

Compressed R,R-formoterol L-tartrate tablets may be prepared using conventional direct compression techniques, such that each dosage unit contains 0.06 mg to 1 mg of formoterol tartrate.

|  | Per tablet | Per 10,000 tablets |
|---|---|---|
| Formoterol tartrate | 0.1 mg | 1 g |
| Microcrystalline Cellulose | 80 mg | 800 g |
| Stearic Acid | 5 mg | 50 g |
| Colloidal Silica | 1 mg | 10 g |

All of the ingredients are blended in a suitable blender. The resulting mixture is compressed into tablets, using a $^9/_{32}$-inch (7 mm) punch.

Example 4

Soft gelatin R,R-formoterol L-tartrate capsules may be prepared with a mixture of formoterol tartrate in a digestible oil such as soybean oil, lecithin, cottonseed oil, or olive oil wherein the mixture is injected by means of a positive pressure pump into gelatin, such that each dosage unit contains 0.06 mg to 1 mg of R,R-formoterol L-tartrate. The capsules are washed and dried.

Example 5

| An example of a suspension for inhalation: | |
|---|---|
|  | Quantity contained in Each Metered Dose Dispenser 7.5 mL (10.5g) Canister |
| (R,R) formoterol L-tartrate | 1.8 mg |
| trichloromonofluoromethane | 5.16 g |
| dichlorodifluoromethane | 5.16 g |
| sorbitan trioleate | 0.105 g |

The metered dose dispenser contains micronized (R,R) formoterol L-tartrate in suspension. Each actuation delivers 6 µg of (R,R) formoterol L-tartrate from the mouthpiece. Each canister provides about 300 inhalations.

An aqueous aerosol formulation for use in a nebulizer may be prepared by dissolving 2 mg of formoterol tartrate in 10 mL of citrate buffered saline, buffered to pH 5. Because of the problematic stability of R,R-formoterol L-tartrate in aqueous solution, this formulation is not attractive for long term storage, but it is quite suitable for short term use. An approach to long-term storage of dosage forms for aqueous aerosols is described in our copending U.S. provisional application No. 60/061,363, filed Oct. 8, 1997, the entire disclosure of which is incorporated herein by reference.

Dry powder inhaler compositions are also well suited for R,R-formoterol L-tartrate. The compositions are made by combining dry lactose having a particle size between 1 µm and 100 µm, preferably 63–90 µm, with micronized formoterol tartrate in a weight ratio of 10:1 and dry blending. The dry powder is loaded into a dry powder dispenser such as that of U.S. Pat. Nos. 5,715,810; 5,529,059 or application Ser. No. 08/780,801, the disclosures of which are incorporated herein by reference.

Oral syrups, as well as other oral liquid formulations, are well known to those skilled in the art, and general methods for preparing them are found in any standard pharmacy school textbook, for example *Remington: The Science and Practice of Pharmacy*. Chapter 86 of the 19th edition of Remington entitled "Solutions, Emulsions, Suspensions and Extracts" describes in complete detail the preparation of syrups (pages 1503–1505) and other oral liquids. The relevant disclosure (Chapter 86) is incorporated herein by reference.

We claim:

1. A process for preparing a compound of formula

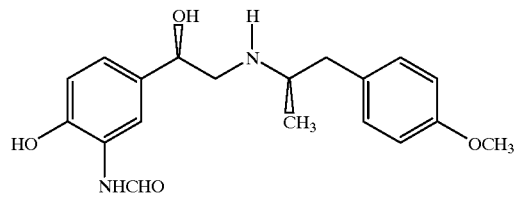

or a salt thereof, comprising the sequential steps of:

(a) reacting a compound of formula

with a compound of formula

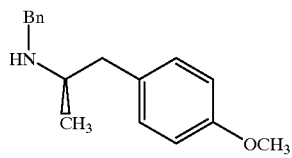

wherein R is benzyl or substituted benzyl, and (b) reducing with a source of hydrogen in the presence of a noble metal catalyst.

2. A process according to claim 1 wherein said compound of formula

is produced in situ from the corresponding bromohydrin

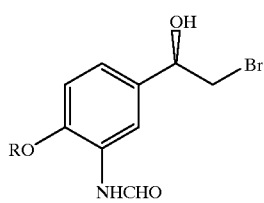

by treatment with a base.

3. A process according to claim 1 wherein said compound of formula

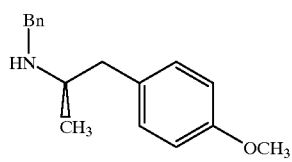

is produced in situ from a corresponding salt by treatment with a base.

4. A process according to claim 1 wherein said compound of formula

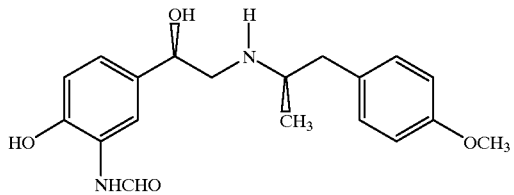

is of the R,R configuration.

5. A process according to claim 1 wherein said compound of formula

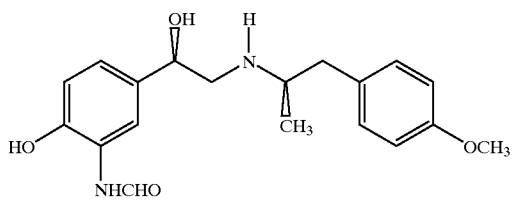

is of the R,S configuration.

6. A process for preparing a compound of formula

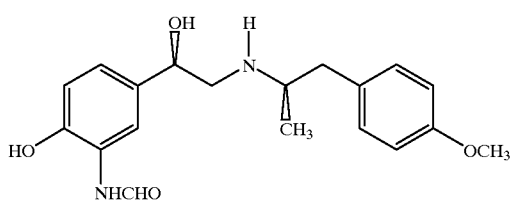

or salt thereof, comprising the sequential steps of:

(a) combining a compound of formula

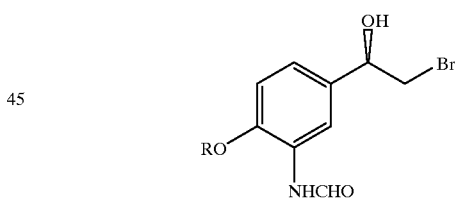

a compound of formula

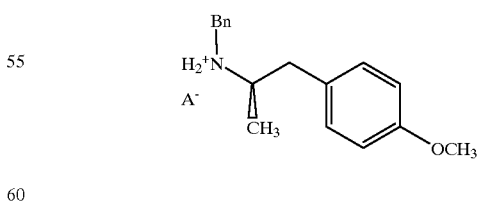

wherein R is benzyl or substituted benzyl and A⁻ is an acid counter ion, and at least one equivalent of a base to produce a mixture comprising an epoxide and a free base;

(b) heating said mixture of an epoxide and a free base at a temperature sufficient to cause a reaction to produce a benzyl-protected aminoalcohol; and (c) reducing said benzyl-protected aminoalcohol with hydrogen gas in the presence of a noble metal catalyst.

7. A process according to any of claims 1, 2, 3, 4 or 6 wherein said noble metal catalyst is palladium.

8. A process according to any of claims 2, 3, or 6 wherein said base is an alkali metal carbonate.

9. A process according to any of claims 1 to 6 wherein said salt is a tartrate salt.

10. A process according to any of claims 1 to 6 wherein said salt is a fumarate salt.

11. A process for synthesizing a compound of formula

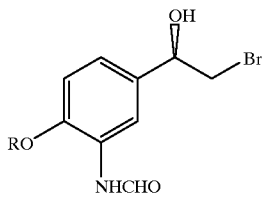

wherein R is benzyl or substituted benzyl, comprising the sequential steps of:

(a) reducing 2-bromo-4'-RO-3'-nitroacetophenone with about one equivalent of a borane reagent in the presence of a catalytic amount of a single enantiomer of an oxazaborolidine reagent to produce substantially enantiomerically pure α-(bromomethyl)-4-RO-3-nitrobenzenemethanol (b) reducing said α-(bromomethyl)-4-RO-3-nitrobenzenemethanol with hydrogen in the presence of a noble metal catalyst to produce an aniline; and (c) formylating said aniline with formic acid and acetic anhydride.

12. A process according to claim 11 wherein said oxazaborolidine reagent is generated in situ from (1R,2S)-1-amino-2-indanol and two equivalents of borane reagent.

13. A process according to claim 11 wherein said noble metal catalyst is platinum and said oxazaborolidine is derived from cis 1-amino-2-indanol.

14. A process according to claim 11 wherein steps (b) and (c) are carried out without isolation of said aniline.

15. A process according to claim 11 wherein said single enantiomer of an oxazaborolidine is derived from (1R,2S)-1-amino-2-indanol, and said substantially enantiomerically pure α-(bromomethyl)-4-RO-3-nitrobenzenemethanol is R-α-(bromomethyl)-4-phenylmethoxy-3-nitrobenzenemethanol.

16. A process for preparing a substantially enantiomerically pure salt of 4-methoxy-α-methyl-N-(phenylmethyl) benzeneethanamine comprising:

(a) reducing 4-methoxyphenyl acetone with hydrogen in the presence of a platinum catalyst and about 1 equivalent of benzylamine in methanol;

(b) adding about one equivalent of a single enantiomer of mandelic acid;

(c) heating to obtain a methanolic solution;

(d) cooling to obtain a crystalline solid phase; and (e) recovering said crystalline solid from said methanolic solution.

17. A process according to claim 16 comprising the additional step of converting said crystalline solid from step (e) to a salt of an acid other than mandelic acid.

18. A process for preparing a compound of formula

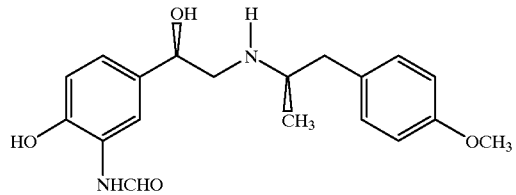

comprising the sequential steps of:

(a) reducing 2-bromo-4'-benzyloxy-3'-nitroacetophenone with about one equivalent of a borane reagent in the presence of a catalytic amount of a single enantiomer of an oxazaborolidine derived from cis 1-amino-2-indanol to produce substantially enantiomerically pure α-(bromomethyl)-4-phenylmethoxy-3-nitrobenzenemethanol:

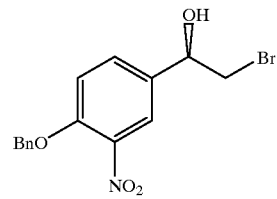

(b) reducing said α-(bromomethyl)-4-phenylmethoxy-3-nitrobenzenemethanol with a source of hydrogen in the presence of a noble metal catalyst to produce an aniline;

(c) formylating said aniline with formic acid and acetic anhydride to produce a compound of formula

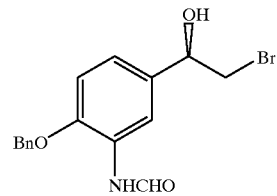

(d) combining said compound of formula

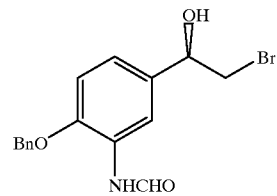

a compound of formula

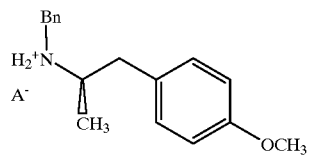

wherein A⁻ is an acid counter ion, and at least one equivalent of a base to produce a mixture comprising an epoxide and a free base;

(e) heating said mixture of an epoxide and a free base at a temperature sufficient to cause a reaction to produce a benzyl-protected aminoalcohol; and (f) reducing said benzyl-protected aminoalcohol with hydrogen gas in the presence of a noble metal catalyst.

19. A compound of formula:

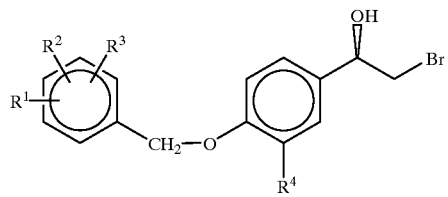

wherein each of $R^1$, $R^2$ and $R^3$ is independently chosen from the group consisting of hydrogen, $C_1$ to $C_6$-alkyl, $C_1$ to $C_6$-alkoxyl, and halogen and $R^4$ is —$NO_2$, —$NH_2$ or —NHCHO.

20. A compound according to claim 19 wherein all of $R^1$, $R^2$ and $R^3$ are hydrogen.

* * * * *